(12) United States Patent
Ishihara et al.

(10) Patent No.: US 10,625,245 B2
(45) Date of Patent: Apr. 21, 2020

(54) METHOD FOR PRODUCING ALCOHOL

(71) Applicant: Kao Corporation, Tokyo (JP)

(72) Inventors: Daisuke Ishihara, Wakayama (JP); Noritatsu Tsubaki, Toyama (JP); Yoshiharu Yoneyama, Toyama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/080,599

(22) PCT Filed: Mar. 29, 2017

(86) PCT No.: PCT/JP2017/012916
§ 371 (c)(1),
(2) Date: Aug. 28, 2018

(87) PCT Pub. No.: WO2017/175638
PCT Pub. Date: Oct. 12, 2017

(65) Prior Publication Data
US 2019/0054452 A1 Feb. 21, 2019

(30) Foreign Application Priority Data
Apr. 4, 2016 (JP) .................... 2016-074920

(51) Int. Cl.
| | | |
|---|---|---|
| *B01J 23/75* | (2006.01) | |
| *B01J 37/08* | (2006.01) | |
| *C07C 31/125* | (2006.01) | |
| *C07C 33/02* | (2006.01) | |
| *B01J 37/02* | (2006.01) | |
| *B01J 35/10* | (2006.01) | |
| *C07C 29/00* | (2006.01) | |
| *C07C 29/50* | (2006.01) | |
| *C07B 61/00* | (2006.01) | |

(52) U.S. Cl.
CPC .............. *B01J 23/75* (2013.01); *B01J 35/10* (2013.01); *B01J 35/108* (2013.01); *B01J 35/1057* (2013.01); *B01J 35/1061* (2013.01); *B01J 37/02* (2013.01); *B01J 37/08* (2013.01); *C07C 29/00* (2013.01); *C07C 29/50* (2013.01); *C07C 31/125* (2013.01); *C07C 33/02* (2013.01); *C07B 61/00* (2013.01)

(58) Field of Classification Search
CPC ......... C07C 29/00; C07C 29/50; C07C 33/02; C10G 2/32; B01J 23/75; B01J 35/1057; B01J 35/1061; B01J 35/108; B01J 37/08; B01J 31/125; B01J 35/10; B01J 37/02
See application file for complete search history.

(56) References Cited

U.S. PATENT DOCUMENTS

| | | |
|---|---|---|
| 4,659,742 A | 4/1987 | Courty et al. |
| 4,751,248 A | 6/1988 | Lin et al. |
| 2005/0107479 A1 | 5/2005 | Espinoza et al. |
| 2010/0093523 A1 | 4/2010 | Jun et al. |
| 2010/0130349 A1 | 5/2010 | Bae et al. |

FOREIGN PATENT DOCUMENTS

| | | |
|---|---|---|
| JP | 54-119385 A | 9/1979 |
| JP | 58-180437 A | 10/1983 |
| JP | 64-26526 A | 1/1989 |
| JP | 1-128948 A | 5/1989 |
| JP | 2006-297286 A | 11/2006 |
| JP | 2010-524681 A | 7/2010 |
| JP | 2010-532245 A | 10/2010 |
| WO | WO 02/00338 A1 | 1/2002 |
| WO | WO 2014/205059 A1 | 12/2014 |

OTHER PUBLICATIONS

Tsubaki et al., Bimodal porous material and catalyst using the same (WO 2002000338 A1 machine translation), Jan. 2002.*
Ding et al., "Copper-Iron Supported Bimodal Pore Catalyst and its Application for Higher Alcohols Synthesis," Catalysis Today, vol. 234, 2014 (published online Feb. 20, 2014) pp. 278-284.
Gao et al., "Core-shell Cu@(CuCo-alloy)/$Al_2O_3$ catalysts for the synthesis of higher alcohols from syngas," Green Chemistry, vol. 17, 2015, pp. 1525-1534 (12 pages total).
International Preliminary Report on Patentability and English translation of the Written Opinion of the International Searching Authority (PCT/IB/373 and PCT/ISA/237) for International Application No. PCT/JP2017/012916, dated Oct. 9, 2018.
Jiao et al., "Effect of $La_2O_3$ doping on syntheses of $C_1$-$C_{18}$ mixed linear α-alcohols syngas over the Co/AC catalysts," Applied Catalysis A: General, vol. 364, 2009 (published onlien May 27, 2009), pp. 137-142 (8 pages total).
Lee et al., "Role of support on higher alchol synthesis from syngas," Applied Catalysis A: General, vol. 480, 2014 (published online Apr. 21, 2014), pp. 128-133 (9 pages total).
Toyoda et al., "Effects of Adding Cobalt and Potassium to $MoS_2$-based Catalysts on Mixed Alcohol Synthesis," Journal of the Japan Petroleum Institute, vol. 57, No. 4, 2014, pp. 171-183.

(Continued)

*Primary Examiner* — Jafar F Parsa

(74) *Attorney, Agent, or Firm* — Birch, Stewart, Kolasch & Birch, LLP

(57) ABSTRACT

A method for producing an alcohol having 8 or more and 22 or less carbon atoms includes the following steps: step 1: forming a porous layer on a surface of a porous material having a pore size mode of 30 nm or more and 200 nm or less to obtain a bimodal carrier; step 2: supporting cobalt on the bimodal carrier obtained in step 1 to obtain a catalyst having peaks of pore distribution in a range of 1 nm or more and 25 nm or less and a range of 30 nm or more and 200 nm or less, respectively; and step 3: reacting carbon monoxide with hydrogen at a gauge pressure of 2 MPa or more and 100 MPa or less in the presence of the catalyst obtained in step 2.

11 Claims, No Drawings

(56) References Cited

OTHER PUBLICATIONS

Wang et al., "Influence of the bimodal pore structure on the CO hydrogenation activity and selectivity of cobalt catalysts," RSC Adv., vol. 5, 2015, pp. 65358-65364.

Yanagihara et al., "Higher alcohol formation under Fischer-Tropsch conditions by cobalt catalysts," Proceedings of Discussion A at Meeting for Discussion of Catalysis, 2012, vol. 109, p. 26 (English abstract only).

European Search Report, dated Oct. 31, 2019, for European Application No. 17779017.7.

Ishida et al., "Synthesis of higher alcohols by Fischer-Tropsch synthesis over alkali metal-modified cobalt catalysts," Applied Catalysis A: General, Elsevier, vol. 458, Amsterdam, NL, May 1, 2013, XP055632154, pp. 145-154.

Tsubaki et al., "A new method of bimodal support preparation and its application in Fischer-Tropsch synthesis," Catalysis Communications, Elsevier, vol. 2, No. 10, Amsterdam, NL, Dec. 1, 2001, XP002427460, pp. 311-315.

Zhang, et al., "Development of bimodal cobalt catalysts for Fischer-Tropsch synthesis," Catalysis Today, Elsevier, vol. 93-95, Amsterdam, NL, Sep. 1, 2004, (Available online Jul. 2, 2004), XP027186001, pp. 55-63.

Extended European Search Report for European Application No. 17779017.7, dated Jan. 24, 2020.

\* cited by examiner

METHOD FOR PRODUCING ALCOHOL

FIELD OF THE INVENTION

The present invention relates to a method for producing an alcohol, and a method for producing a catalyst for producing an alcohol.

BACKGROUND OF THE INVENTION

An alcohol having 8 or more and 22 or less carbon atoms are suitably used as an intermediate material of chemicals such as surfactants. As a method for producing a higher alcohol from a syngas as a raw material, a method for producing a higher alcohol including synthesizing an olefin by the Fischer-Tropsch synthesis (hereinafter referred to also as the FT synthesis), and subsequent hydroformylation and hydrogenation is known. However, the synthesis via olefination has many steps, and the target alcohol having 8 or more and 22 or less carbon atoms cannot be obtained at a high yield.

In Catalysis Today 234 (2014) 278-284 (Non-Patent Literature 1), as a method for producing an alcohol from a syngas, a method for synthesizing an alcohol directly from a syngas with use of a catalyst obtained by supporting Cu and Fe on a bimodal carrier of silicon oxide is disclosed.

In the Royal Society of Chemistry Advances 5 (2015) 65358-65364 (Non-Patent Literature 2), a method for synthesizing a long-chain hydrocarbon by the FT synthesis with use of a catalyst with cobalt supported on a silica carrier having two pore size peaks in a mesopore region is disclosed.

In WO-A 2002/00338 (Patent Literature 1), a method for synthesizing a hydrocarbon with use of a catalyst with cobalt supported on a bimodal carrier of silicon oxide is disclosed.

SUMMARY OF THE INVENTION

However, in Non-Patent Literature 1, a long-chain alcohol having 8 or more carbon atoms suitably used as an intermediate material of chemicals such as surfactants is not obtained. In Non-Patent Literature 2, although a method for synthesizing a long-chain hydrocarbon is disclosed, a method for synthesizing a long-chain alcohol and a method for forming a microscopic pore inside a pore of a porous material are not disclosed. Also, in Patent Literature 1, although a method for synthesizing a hydrocarbon is disclosed, no long-chain alcohol is obtained.

The present invention provides a method for producing an alcohol capable of selectively obtaining a target alcohol having 8 or more and 22 or less carbon atoms in one step from a syngas as a raw material, and a method for producing a catalyst for producing an alcohol. Being capable of selectively obtaining an alcohol having 8 or more and 22 or less carbon atoms referred to here specifically means that an alcohol having 8 or more and 22 or less carbon atoms can be preferentially obtained compared to an alcohol having a different number of carbon atoms from the above.

The present invention relates to a method for producing an alcohol having 8 or more and 22 or less carbon atoms including the following steps:

step 1: forming a porous layer on a surface of a porous material having a pore size mode of 30 nm or more and 200 nm or less to obtain a bimodal carrier;

step 2: supporting cobalt on the bimodal carrier obtained in step 1 to obtain a catalyst having peaks of pore distribution in a range of 1 nm or more and 25 nm or less and a range of 30 nm or more and 200 nm or less, respectively; and step 3: reacting carbon monoxide with hydrogen at a gauge pressure of 2 MPa or more and 100 MPa or less in the presence of the catalyst obtained in step 2.

In addition, the present invention relates to a method for producing a catalyst for use in producing an alcohol having 8 or more and 22 or less carbon atoms including the step of reacting carbon monoxide with hydrogen at a gauge pressure of 2 MPa or more and 100 MPa or less, the method including the following steps:

step 1: forming a porous layer on a surface of a porous material having a pore size mode of 30 nm or more and 200 nm or less to obtain a bimodal carrier; and step 2: supporting cobalt on the bimodal carrier obtained in step 1 to obtain a catalyst having peaks of pore distribution in a range of 1 nm or more and 25 nm or less and a range of 30 nm or more and 200 nm or less, respectively.

Furthermore, the present invention relates to a method for producing an alcohol having 8 or more and 22 or less carbon atoms including the step of reacting carbon monoxide with hydrogen at a gauge pressure of 2 MPa or more and 100 MPa or less in the presence of the catalyst obtained by the method for producing a catalyst described above. In other words, the present invention relates to a method for producing an alcohol having 8 or more and 22 or less carbon atoms including the step of reacting carbon monoxide with hydrogen in the presence of the catalyst obtained by the following steps 1 and 2:

step 1: forming a porous layer on a surface of a porous material having a pore size mode of 30 nm or more and 200 nm or less to obtain a bimodal carrier; and step 2: supporting cobalt on the bimodal carrier obtained in step 1 to obtain a catalyst having peaks of pore distribution in a range of 1 nm or more and 25 nm or less and a range of 30 nm or more and 200 nm or less, respectively.

According to the present invention, a method for producing an alcohol capable of selectively obtaining a long-chain alcohol having 8 or more and 22 or less carbon atoms in one step from a syngas as a raw material, and a method for producing a catalyst for producing an alcohol can be provided. Also, according to the method for producing an alcohol of the present invention, a long-chain alcohol having 8 or more and 22 or less carbon atoms suitably used as a base of surfactants and an intermediate material of various compounds can be selectively produced from a syngas in one step.

EMBODIMENTS OF THE INVENTION

<Catalyst>

The catalyst used in the present invention is a catalyst obtained by supporting cobalt as a catalytic metal on a bimodal carrier obtained by forming a porous layer on a surface of a porous material having a pore size mode of 30 nm or more and 200 nm or less, and having peaks of pore distribution in a range of 1 nm or more and 25 nm or less and a range of 30 nm or more and 200 nm or less, respectively.

The bimodal carrier of the present invention referred to here means a porous carrier having both of large pores with a relatively large pore size and small pores with a relatively small pore size, with a dual pore structure having the small pores inside the large pores. Also, the surface of the porous material includes an outer surface of the porous material and an internal surface of the pores.

The bimodal carrier for use in the present invention includes a porous material and a porous layer formed on the surface of the porous material.

The compound constituting the porous material is preferably one or two or more selected from silicon oxide, a silicate, aluminum oxide and titanium oxide, more preferably one or two or more selected from silicon oxide, a silicate, aluminum oxide, further preferably silicon oxide, a silicate or aluminum oxide, and furthermore preferably silicon oxide from the viewpoint of obtaining a bimodal carrier.

The pore size mode of a porous material is 30 nm or more, preferably 40 nm or more, more preferably 50 nm or more, furthermore preferably 55 nm or more, and furthermore preferably 60 nm or more from the viewpoint of accelerating the diffusion of the raw material inside a catalyst and thereby improving the catalytic activity, and 200 nm or less, preferably 100 nm or less, more preferably 80 nm or less, further preferably 75 nm or less, and furthermore preferably 70 nm or less from the viewpoint of maintaining the strength of a catalyst.

The compounds to constitute a porous layer are preferably one or two or more selected from a silicate, silicon oxide, aluminum oxide and zirconium oxide, more preferably one or two or more selected from a silicate and aluminum oxide, further preferably a silicate or aluminum oxide, furthermore preferably a silicate, and furthermore preferably zirconium silicate from the viewpoint of improving the catalytic activity.

The bimodal carrier for use in the present invention has peaks in a pore size (hereinafter referred to also as D) distribution in a range of 1 nm or more and 25 nm or less (hereinafter referred to as small pore range) and a range of 30 nm or more and 200 nm or less (hereinafter referred to as large pore range), respectively.

The pores of a bimodal carrier and a catalyst for use in the present invention referred to here are pores having a pore volume (hereinafter referred to also as V) of 0.02 mL/g or more.

Also, the pore distribution of the present invention is a distribution obtained by plotting the quotient of the differential pore volume (dV) divided by the differential logarithmic value (d(log D)) of pore size(hereinafter referred to also as D), i.e., (dV/d(log D)), against D (hereinafter referred to also as Log differential pore volume distribution).

Also, the peak of pore distribution of the present invention means the pore size having the largest dV/d(log D) in each of the two ranges.

The small pore range of the pore distribution of the bimodal carrier of the present invention is mainly derived from the porous layer, and the peak position lies at 1 nm or more, preferably 2 nm or more, and more preferably 3 nm or more from the viewpoint of improving the catalytic activity by adsorption of the raw material on the surface of a catalyst having pores larger than the molecular size of the raw material, and at 25 nm or less, preferably 20 nm or less, more preferably 15 nm or less, further preferably 12 nm or less, furthermore preferably 10 nm or less, furthermore preferably 8 nm or less, furthermore preferably 6 nm or less, and furthermore preferably 5 nm or less from the viewpoint of the easy progress in increasing the number of carbon atoms of hydrocarbon groups (hereinafter referred to also as carbon-chain propagation) by re-adsorption of short-chain products.

The large pore range of the pore distribution of the bimodal carrier for use in the present invention is mainly derived from the pore material, and the peak position thereof lies at 30 nm or more, preferably 40 nm or more, more preferably 50 nm or more, and further preferably 55 nm or more from the viewpoint of accelerating the diffusion of the raw material gas inside the catalyst and thereby improving the catalytic activity, and 200 nm or less, preferably 100 nm or less, more preferably 75 nm or less, and further preferably 65 nm or less from the viewpoint of maintaining the strength of the catalyst.

The bimodal carrier for use in the present invention as a whole of the bimodal carrier has a pore volume of preferably 0.2 mL/g or more, more preferably 0.4 mL/g or more, further preferably 0.5 mL/g or more, furthermore preferably 0.6 mL/g or more, and furthermore preferably 0.7 mL/g or more from the viewpoint of improving the catalytic activity, and preferably 1.5 mL/g or less, more preferably 1 mL/g or less, and further preferably 0.9 mL/g or less from the viewpoint of maintaining the strength of the catalyst.

The peak position of pore distribution in the small pore range or the large pore range of the bimodal carrier for use in the present invention and the pore volume of the bimodal carrier as a whole may be measured by a gas adsorption method.

Specific examples of the gas adsorption method include a nitrogen adsorption method using nitrogen as adsorption gas, an argon adsorption method using argon as adsorption gas, and a helium adsorption method using helium as adsorption gas, and the nitrogen adsorption method is preferred from the viewpoint of achieving simple measurement. The method is more specifically described in Examples.

The catalyst for use in the present invention contains cobalt as catalytic metal supported on a bimodal carrier.

The content of cobalt as catalytic metal in the catalyst as a whole for use in the present invention is preferably 0.1 mass % or more, more preferably 1 mass % or more, further preferably 5 mass % or more, and furthermore preferably 7 mass % or more from the viewpoint of improving the catalytic activity, and preferably 50 mass % or less, more preferably 20 mass % or less, further preferably 15 mass % or less, and furthermore preferably 10 mass % or less from the viewpoint of economic efficiency.

The catalytic metal may contain a metal other than cobalt as a promoter component from the viewpoint of suppressing the hydrogenation of an olefin and accelerating the generation of an alcohol. From the viewpoint of suppressing the hydrogenation of an olefin and accelerating the generation of an alcohol, the promoter component is preferably one or two or more selected from metals in the first to seventh groups and metals in the ninth to twelfth group other than cobalt, more preferably one or two or more selected from alkaline metals, alkaline earth metals, rare earths, and transition metals other than cobalt, further preferably one or two or more selected from lithium, sodium, potassium, cesium, magnesium, calcium, strontium, barium, scandium, lanthanum, zirconium, niobium, molybdenum, manganese, tungsten, rhenium, rhodium, iridium, palladium, platinum, copper, silver and zinc, and furthermore preferably one or two or more selected from sodium, potassium, lanthanum, zirconium, molybdenum, manganese and copper.

The catalyst for use in the present invention has peaks of pore distribution in a small pore range and a large pore range, respectively.

The catalyst for use in the present invention allows a target long-chain alcohol having 8 or more and 22 or less carbon atoms to be selectively obtained in one-step reaction from a syngas of hydrogen and carbon monoxide as a raw material. Although the mechanism of the effect is not necessarily known, it is supposed that in the large pore range, the diffusion of hydrogen and carbon monoxide as the raw material gases is enhanced to achieve a high efficiency in generation of an alcohol through the promoted contact with a catalyst metal, and in the small pore range, a short-chain product having a short carbon chain in the generated alcohol is adsorbed to cause a carbon-chain propagation through further reaction with the raw material gases, so that the target long-chain alcohol can be obtained.

The small pore range of the pore distribution of the catalyst for use in the present invention is mainly derived from the porous layer, and the peak position ($d_1$) lies at 1 nm or more, preferably 3 nm or more, more preferably 4 nm or more, further preferably 5 nm or more, and furthermore preferably 6 nm or more from the viewpoint of improving the catalytic activity by adsorption of short-chain products on the surface of a catalyst having pores larger than the molecular size of the short-chain products, and at 25 nm or less, preferably 20 nm or less, more preferably 15 nm or less, further preferably 14 nm or less, furthermore preferably 12 nm or less, furthermore preferably 10 nm or less, and furthermore preferably 8 nm or less from the viewpoint of easily accelerating the chain growth by re-adsorption of the short-chain products.

The total of pore volume of the pores forming peaks of pore distribution in the small pore range of the pore distribution of the catalyst for use in the present invention (hereinafter referred to also as pore volume ($V_1$) in small pore range) is preferably 0.02 mL/g or more, more preferably 0.06 mL/g or more, further preferably 0.1 mL/g or more, furthermore preferably 0.14 mL/g or more, and furthermore preferably 0.17 mL/g or more from the viewpoint of improving the catalytic activity by adsorbing the raw material to the catalyst surface with the pore of the catalyst larger than the molecular size of the raw material to be adsorbed, and preferably 0.5 mL/g or less, more preferably 0.3 mL/g or less, further preferably 0.2 mL/g or less, and furthermore preferably 0.19 mL/g or less from the viewpoint of easily accelerating the chain growth by re-adsorption of the short-chain products.

Incidentally, the pore volume ($V_1$) in the small pore range is a value calculated from the integration of the volume of pores present between two points that are the peak rise and the peak fall in the pore distribution in the small pore range.

The large pore range of the pore distribution of the catalyst for use in the present invention is mainly derived from the porous layer, and the peak position ($d_2$) lies at 30 nm or more, preferably 40 nm or more, more preferably 50 nm or more, and further preferably 55 nm or more from the viewpoint of improving the catalytic activity by accelerating the diffusion of the raw material gas inside the catalyst, and at 200 nm or less, preferably 100 nm or less, more preferably 70 nm or less, and further preferably 65 nm or less from the viewpoint of maintaining the strength of the catalyst.

The total of pore volume of the pores forming a peak of pore distribution in the large pore range of the pore distribution of the catalyst for use in the present invention (hereinafter referred to also as pore volume ($V_2$) in large pore range) is preferably 0.1 mL/g or more, more preferably 0.3 mL/g or more, further preferably 0.4 mL/g or more, and furthermore preferably 0.45 mL/g or more from the viewpoint of improving the catalytic activity, and preferably 1 mL/g or less, more preferably 0.8 mL/g or less, further preferably 0.7 mL/g or less, furthermore preferably 0.6 mL/g or less, and furthermore preferably 0.55 mL/g or less from the viewpoint of maintaining the strength of the catalyst.

Incidentally, the pore volume ($V_2$) in the large pore range is a value calculated from the integration of the volume of pores present between two points that are the peak rise and the peak fall in the pore distribution in the large pore range.

In the pore distribution of the catalyst for use in the present invention, the ratio of the peak position in the small pore range ($d_1$) to the peak position in the large pore range ($d_2$), i.e., $d_1/d_2$, is preferably 0.01 or more, more preferably 0.05 or more, and further preferably 0.1 or more from the viewpoint of improving the catalytic activity, and preferably 0.8 or less, more preferably 0.4 or less, further preferably 0.19 or less, and furthermore preferably 0.12 or less from the similar viewpoint.

In the pore distribution of the catalyst for use in the present invention, the ratio of the pore volume in the small pore range ($V_1$) to the pore volume in the large pore range ($V_2$), i.e., $V_1/V_2$, is preferably 0.02 or more, more preferably 0.05 or more, further preferably 0.1 or more, and furthermore preferably 0.3 or more from the viewpoint of improving the catalytic activity, and preferably 5 or less, more preferably 1 or less, further preferably 0.5 or less, furthermore preferably 0.38 or less, and furthermore preferably 0.35 or less from the similar viewpoint.

The pore volume of the catalyst for use in the present invention as a whole of the catalyst is preferably 0.2 mL/g or more, more preferably 0.4 mL/g or more, further preferably 0.5 mL/g or more, furthermore preferably 0.6 mL/g or more, and furthermore preferably 0.7 mL/g or more from the viewpoint of improving the catalytic activity, and preferably 1.5 mL/g or less, more preferably 1 mL/g or less, and further preferably 0.9 mL/g or less from the viewpoint of maintaining the strength of the catalyst.

The specific surface area of the catalyst for use in the present invention as a whole of the catalyst is preferably 10 $m^2/g$ or more, more preferably 100 $m^2/g$ or more, further preferably 200 $m^2/g$ or more, and furthermore preferably 230 $m^2/g$ or more from the viewpoint of improving the catalytic activity, and preferably 1000 $m^2/g$ or less, more preferably 500 $m^2/g$ or less, and further preferably 300 $m^2/g$ or less from the viewpoint of maintaining the strength of the catalyst.

The catalytic metal content in the catalyst for use in the present invention can be measured by high-frequency inductively coupled plasma emission spectrophotometry (referred to also as ICP-AEP). The method is more specifically described in Examples.

The peak position of pore distribution and the pore volume in the small pore range or the large pore range of the catalyst for use in the present invention and the pore volume and the specific surface area of the catalyst as a whole may be measured by a gas adsorption method.

Specific examples of the gas adsorption method include a nitrogen adsorption method using nitrogen as adsorption gas, an argon adsorption method using argon as adsorption gas, and a helium adsorption method using helium as adsorption gas, and the nitrogen adsorption method is preferred from the viewpoint of achieving simple measurement. The method is more specifically described in Examples.

<Method for Producing Catalyst>

A method for producing a catalyst of the present invention includes the following steps:

step 1: forming a porous layer on a surface of a porous material having a pore size mode of 30 nm or more and 200 nm or less to obtain a bimodal carrier; and step 2: supporting cobalt on the bimodal carrier obtained in step 1 to obtain a catalyst having peaks of pore distribution in a range of 1 nm or more and 25 nm or less and a range of 30 nm or more and 200 nm or less, respectively.

The description in <Catalyst> mentioned above may be appropriately applied to the method for producing a catalyst of the present invention.

Preferably, step 1 includes the following step 1-1 and step 1-2:

step 1-1: supporting a dispersion or a solution containing a raw material of the porous layer on the porous material; and step 1-2: calcining the porous material with the dispersion or the solution supported thereon obtained in step 1-1.

Step 1-1 is a step of impregnating the porous material with a dispersion or a solution containing a raw material of the porous layer, so as to support the raw material of the porous layer on the porous material.

The dispersion or the solution containing the raw material of the porous layer is preferably a sol, a slurry or a solution, and more preferably a sol from the viewpoint of more easily forming pores in a small pore range.

Supporting of a raw material of the porous layer in step 1-1 is performed preferably by the Incipient Wetness method (hereinafter referred to also as the IW method) from the viewpoint of selectively forming the porous layer in the pores of the porous material by preventing the raw material of the porous layer from aggregating outside the pores of the porous material and by efficiently supplying the raw material of the porous layer into the pores of the porous material.

Incidentally, the IW method is a method of impregnating a carrier with a solution containing a component to be supported such that the solution is absorbed into the carrier, with the total volume of the solution being the same as the total pore volume of the carrier.

The raw material of the porous layer is preferably one or two or more selected from a silicate, silicon oxide, aluminum oxide and zirconium oxide, more preferably one or two or more selected from a silicate and aluminum oxide, further preferably a silicate or aluminum oxide, furthermore preferably a silicate, and furthermore preferably zirconium silicate from the viewpoint of improving the catalytic activity.

A solvent of the dispersion or the solution containing the raw material of the porous layer is preferably one or two or more selected from alcohols having 1 or more and 4 or less carbon atoms and water, more preferably an alcohol having 1 or more and 4 or less carbon atoms, further preferably an alcohol having 2 or more and 3 or less carbon atoms, furthermore preferably an alcohol having 3 carbon atoms, and furthermore preferably isopropanol from the viewpoint of easy availability.

The dispersion or the solution containing the raw material of the porous layer may contain an organic compound from the viewpoint of harmonizing the peak position in the small pore range of the pore distribution with the molecular size of the short-chain products to be adsorbed.

The organic compound is preferably one or two or more selected from a polymer or a surfactant, more preferably one or two or more selected from a polymer, further preferably one or more selected from a polyalkylene glycol, furthermore preferably one or two or more selected from a block copolymer of polyoxyethylene and polyoxypropylene, and furthermore preferably one or two or more selected from a ternary block copolymer of polyoxyethylene, polyoxypropylene and polyoxyethylene from the viewpoint of harmonizing the peak position in the small pore range of the pore distribution with the molecular size of the short-chain products to be adsorbed.

The weight average molecular weight of the polymer is preferably 100 or more, more preferably 400 or more, further preferably 1000 or more, furthermore preferably 3000 or more, and furthermore preferably 5000 or more from the viewpoint of balancing the size of sol particles with the molecular size of the short-chain products to be adsorbed, and preferably 10000 or less, more preferably 7000 or less, further preferably 6500 or less, and furthermore preferably 6000 or less from the viewpoint of balancing the upper limit of the pore size in the small pore range of the pore distribution with the molecular size of the short-chain products to be adsorbed.

In the case where the polymer is a block copolymer of polyoxyethylene and polyoxypropylene, the weight average molecular weight can be obtained by gel permeation chromatography using tetrahydrofuran, a liquid mixture of water/methanol/acetic acid/sodium acetate, or the like as an eluent, with polyethylene glycol as a standard material.

The content of the raw material of the porous layer in a dispersion or a solution containing the raw material of the porous layer is preferably 1 mass % or more, more preferably 10 mass % or more, further preferably 15 mass % or more, and furthermore preferably 20 mass % or more from the viewpoint of selectively forming the porous layer in pores, and preferably 50 mass % or less, more preferably 30 mass % or less, further preferably 25 mass % or less, and furthermore preferably 22 mass % or less from the viewpoint of easiness for a sol to enter inside the pores of a porous material.

The mass ratio of the raw material of the porous layer in a dispersion or a solution containing the raw material of the porous layer relative to 100 parts by mass of the porous material is preferably 1 part by mass or more, more preferably 10 parts by mass or more, further preferably 20 parts by mass, furthermore preferably 30 mass % or more, and furthermore preferably 35 mass % or more from the viewpoint of selectively forming the porous layer inside the pores, and preferably 50 parts by mass or less, and more preferably 40 parts by mass or less from the viewpoint of easiness for a sol to enter inside the pores of a porous material.

The content of the organic compound in a dispersion or a solution containing the raw material of the porous layer is preferably 40 mass % or less, more preferably 20 mass % or less, further preferably 10 mass % or less, furthermore preferably 6 mass % or less, and furthermore preferably 1 mass % or less from the viewpoint of sol stability.

When the porous material is impregnated with a dispersion or a solution containing the raw material of the porous layer, the temperature of the dispersion or the solution is preferably 0° C. or more, more preferably 5° C. or more, further preferably 10° C. or more, and furthermore preferably 15° C. or more from the viewpoint of sol stability, and preferably 70° C. or less, more preferably 60° C. or less, further preferably 50° C. or less, furthermore preferably 40° C. or less, and furthermore preferably 35° C. or less from the viewpoint of preventing the evaporation of the solvent.

When the porous material is impregnated with a dispersion or a solution containing the raw material of the porous layer, the pressure in absolute pressure is preferably 10 kPa or more, more preferably 30 kPa or more, further preferably 50 kPa or more, and furthermore preferably 75 kPa or more from the viewpoint of preventing the evaporation of the solvent, and preferably 200 kPa or less, more preferably 150 kPa or less, and further preferably 125 kPa or less from the viewpoint of operability and easiness for a sol to enter into the pores.

When the porous material is impregnated with a dispersion or a solution containing the raw material of the porous layer, it is suitable that the impregnation is performed while stirring with ultrasonic waves or a stirring bar.

Step 1-2 is a step of calcining a bimodal carrier with the dispersion or the solution supported on the porous material in step 1-1 described above.

The calcining temperature is preferably 150° C. or more, more preferably 200° C. or more, further preferably 250° C. or more, furthermore preferably 300° C. or more, and furthermore preferably 400° C. or more from the viewpoint of forming a network among the constituent compounds of a porous material, and preferably 1000° C. or less, more preferably 900° C. or less, further preferably 800° C. or less, furthermore preferably 700° C. or less, and furthermore preferably 600° C. or less from the viewpoint of stability of the raw material of a catalyst.

The calcining is preferably performed under an oxygen-containing atmosphere, and more preferably under air atmosphere from the viewpoint of removing an organic material.

The time for the calcining is preferably 0 hour or more, more preferably 0.5 hours or more, further preferably 1 hour or more, and furthermore preferably 1.5 hours or more from the viewpoint of forming a network among the constituent compounds of a porous material, and preferably 10 hours or less, more preferably 8 hours or less, further preferably 6 hours or less, furthermore preferably 4 hours or less, and furthermore preferably 2.5 hours or less from the viewpoint of stability of the raw material of a catalyst.

Step 2 is a step of supporting cobalt as a catalytic metal on the bimodal carrier obtained in step 1 described above to obtain a catalyst having peaks of pore distribution in a range of 1 nm or more and 25 nm or less and a range of 30 nm or more and 200 nm or less, respectively.

As the method for supporting cobalt as a catalytic metal on the bimodal carrier, a method of impregnating the bimodal carrier with a dispersion or a solution containing a cobalt compound is suitable. The dispersion or the solution containing a cobalt compound is preferably a solution, a sol, or a slurry, and more preferably a solution from the viewpoint of supporting cobalt on the bimodal carrier.

Supporting of cobalt on the bimodal carrier is performed preferably by the IW method from the viewpoint of supporting the cobalt compound inside the pores having a pore size in the small pore range in a highly dispersed state by preventing the cobalt compound from aggregating outside the pores having a pore size in the small pore range and by efficiently supplying the raw material of the porous layer into the pores of the porous material.

The cobalt compound is preferably one or two or more selected from cobalt nitrate, cobalt acetate, cobalt sulfate, cobalt chloride, cobalt bromide, cobalt iodide and cobalt oxide, more preferably one or more selected from cobalt nitrate and cobalt acetate, and further preferably cobalt nitrate from the viewpoint of availability.

The dispersion or the solution may contain a metal other than cobalt as a promoter component. The promoter component is a metal described above, which is preferably contained in the dispersion or the solution as one or two or more metal compounds selected from a nitrate, a acetate, a sulfate and a halogen compound from the viewpoint of availability.

A solvent in the dispersion or the solution is preferably a solvent which dissolves a cobalt compound or a compound of metal other than cobalt, and more preferably an organic solvent or water from the viewpoint of solubility.

The cobalt metal concentration in the dispersion or the solution is preferably 5 mass % or more, more preferably 7 mass % or more, further preferably 8 mass % or more, furthermore preferably 9 mass % or more, and furthermore preferably 10 mass % or more from the viewpoint of selectively supplying cobalt metal into the pores, and preferably 30 mass % or less, more preferably 25 mass % or less, further preferably 20 mass % or less, and furthermore preferably 15 mass % or less from the viewpoint of solubility of the cobalt compound.

When the bimodal carrier is impregnated with the dispersion or the solution, the temperature is preferably 0° C. or more, more preferably 5° C. or more, further preferably 10° C. or more, and furthermore preferably 15° C. or more from the viewpoint of stability of the dispersion or the solution, and preferably 110° C. or less, more preferably 90° C. or less, further preferably 70° C. or less, furthermore preferably 50° C. or less, and furthermore preferably 35° C. or less from the viewpoint of preventing the evaporation of the solvent in the dispersion or the solution.

When the bimodal carrier is impregnated with the dispersion or the solution, the pressure in absolute pressure is preferably 10 kPa or more, more preferably 30 kPa or more, further preferably 50 kPa or more, and furthermore preferably 75 kPa or more from the viewpoint of preventing the evaporation of the solvent in the dispersion or the solution, and preferably 200 kPa or less, more preferably 150 kPa or less, and further preferably 125 kPa or less from the viewpoint of operability and easiness for a sol to enter into the pores.

When the bimodal carrier is impregnated with the dispersion or the solution, it is suitable that the impregnation is performed while stirring with ultrasonic waves or a stirring bar.

After the bimodal carrier is impregnated with the dispersion or the solution, it is suitable that the bimodal carrier is calcined from the viewpoint of improving the catalytic activity.

The temperature for the calcining is preferably 150° C. or more, more preferably 200° C. or more, further preferably 250° C. or more, and furthermore preferably 300° C. or more from the viewpoint of improving the catalytic activity, and preferably 800° C. or less, more preferably 700° C. or less, further preferably 600° C. or less, and furthermore preferably 500° C. or less from the similar viewpoint.

The calcining is performed preferably under an oxygen-containing atmosphere, and more preferably under an air atmosphere from the viewpoint of removing an organic material.

The time for the calcining is preferably 0 hour or more, more preferably 0.5 hours or more, further preferably 1 hour or more, and furthermore preferably 1.5 hours or more from the viewpoint of improving the catalytic activity, and preferably 10 hours or less, more preferably 8 hours or less, further preferably 6 hours or less, furthermore preferably 4 hours or less, and furthermore preferably 2.5 hours or less from the similar viewpoint.

After the calcining, it is suitable to reduce the catalyst with use of a reducing agent from the viewpoint of improving the catalytic activity.

The reducing agent for reducing the catalyst is preferably a mixed gas of carbon monoxide and hydrogen or a hydrogen gas, and more preferably a hydrogen gas from the viewpoint of improving the catalytic activity.

The temperature for reducing the catalyst is preferably 150° C. or more, more preferably 200° C. or more, further preferably 250° C. or more, and furthermore preferably 300° C. or more from the viewpoint of improving the catalytic activity, and preferably 800° C. or less, more preferably 700° C. or less, further preferably 600° C. or less, and furthermore preferably 500° C. or less from the similar viewpoint.

The time for reducing the catalyst is preferably 0 hour or more, more preferably 2 hours or more, further preferably 4 hours or more, furthermore preferably 6 hours or more, and furthermore preferably 8 hours or more from the viewpoint of improving the catalytic activity, and preferably 24 hours or less, more preferably 18 hours or less, further preferably 15 hours or less, and furthermore preferably 12 hours or less from the similar viewpoint.

<Method for Producing Alcohol>

A method for producing an alcohol of the present invention is a method for obtaining an alcohol having 8 or more and 22 or less carbon atoms including the following steps:

step 1: forming a porous layer on a surface of a porous material having a pore size mode of 30 nm or more and 200 nm or less to obtain a bimodal carrier;

step 2: supporting cobalt on the bimodal carrier obtained in step 1 to obtain a catalyst having peaks of pore distribution in a range of 1 nm or more and 25 nm or less and a range of 30 nm or more and 200 nm or less, respectively; and step 3: reacting carbon monoxide with hydrogen at a gauge pressure of 2 MPa or more and 100 MPa or less in the presence of the catalyst obtained in step 2.

The method for producing an alcohol of the present invention is a method for producing an alcohol having 8 or more and 22 or less carbon atoms including a step of reacting carbon monoxide with hydrogen at a gauge pressure of 2 MPa or more and 100 MPa or less in the presence of the catalyst obtained in steps 1 and 2. In other words, the method for producing an alcohol of the present invention is a method for producing an alcohol having 8 or more and 22 or less carbon atoms including the step of reacting carbon monoxide with hydrogen at a gauge pressure of 2 MPa or more and 100 MPa or less in the presence of the catalyst obtained by the above <Method for Producing Catalyst>.

step 1: forming a porous layer on a surface of a porous material having a pore size mode of 30 nm or more and 200 nm or less to obtain a bimodal carrier; and step 2: supporting cobalt on the bimodal carrier obtained in step 1 to obtain a catalyst having peaks of pore distribution in a range of 1 nm or more and 25 nm or less and a range of 30 nm or more and 200 nm or less, respectively.

In the method for producing an alcohol of the present invention, step 1 and step 2 can appropriately apply the matters described in <Catalyst> and <Method for Producing Catalyst>.

In the reaction of step 3 or the reaction of carbon monoxide with hydrogen, from the viewpoints of a raw material composition and productivity, a supply molar ratio $H_2/CO$ of hydrogen gas to carbon monoxide gas which are raw material gases is preferably 0.8 or more, more preferably 1.0 or more, further preferably 1.3 or more, furthermore preferably 1.6 or more, and furthermore preferably 1.8 or more. From the same viewpoints, the supply molar ratio $H_2/CO$ is preferably 2.5 or less, more preferably 2.4 or less, further preferably 2.3 or less, and furthermore preferably 2.2 or less.

From the viewpoint of the simplification of the apparatus, the apparatus in the reaction is preferably a slurry-phase reactor or a fixed-bed reactor, and more preferably a slurry-phase reactor.

From the viewpoint of improving the selectivity of the alcohol, the gauge pressure in the reaction is 2 MPa or more, preferably 3 MPa or more, more preferably 4 MPa or more, further preferably 5 MPa or more, and furthermore preferably 5.5 MPa or more. From the viewpoint of reducing loads to apparatus facilities, the gauge pressure is 100 MPa or less, preferably 50 MPa or less, more preferably 30 MPa or less, further preferably 10 MPa or less, and furthermore preferably 7 MPa or less.

From the viewpoint of improving the reactivity, a temperature in the reaction is preferably 100° C. or more, more preferably 150° C. or more, further preferably 200° C. or more, and furthermore preferably 230° C. or more. From the viewpoint of improving the selectivity of the alcohol, the temperature is preferably 300° C. or less, more preferably 280° C. or less, further preferably 260° C. or less, and furthermore preferably 250° C. or less.

In the reaction, from the viewpoint of the production stability, atmospheric gas other than the raw material gases is preferably inert gas, more preferably nitrogen gas or rare gas, further preferably rare gas, and furthermore preferably argon.

In the reaction, from the viewpoint of the usefulness of a reaction product, the content of the alcohol having 8 or more and 22 or less carbon atoms relative to the whole reaction product is preferably 3% by mass or more, more preferably 4% by mass or more, and further preferably 5% by mass or more. From the viewpoint of the production efficiency, the content is preferably 100% by mass or less, more preferably 50% by mass or less, further preferably 10% by mass or less, and furthermore preferably 7% by mass or less.

The present invention further discloses the following method for producing a catalyst for producing an alcohol and method for producing an alcohol, which are related to the above-mentioned embodiment.

<1>

A method for producing a catalyst for use in producing an alcohol having 8 or more and 22 or less carbon atoms including the step of reacting carbon monoxide with hydrogen at a gauge pressure of 2 MPa or more and 100 MPa or less, the method including the following steps:

step 1: forming a porous layer on a surface of a porous material having a pore size mode of 30 nm or more and 200 nm or less to obtain a bimodal carrier; and step 2: supporting cobalt on the bimodal carrier obtained in step 1 to obtain a catalyst having peaks of pore distribution in a range of 1 nm or more to 25 nm or less and a range of 30 nm or more to 200 nm or less, respectively.

<2>

The method for producing a catalyst according to the above <1>, wherein the constituent compound of the porous material is one or two or more selected from silicon oxide, a silicate, aluminum oxide, and titanium oxide, preferably one or two or more selected from silicon oxide, a silicate, and aluminum oxide, more preferably silicon oxide, a silicate, or aluminum oxide, and further preferably silicon oxide.

<3>

The method for producing a catalyst according to the above <1> or <2>, wherein the pore size mode of the porous material is 40 nm or more, preferably 50 nm or more, more preferably 55 nm or more, and further preferably 60 nm or more, and is 100 nm or less, preferably 80 nm or less, more preferably 75 nm or less, and further preferably 70 nm or less.

<4>

The method for producing a catalyst according to any one of the above <1> to <3>, wherein the constituent compound of the porous layer is one or two or more selected from a silicate, silicon oxide, aluminum oxide, and zirconium oxide, preferably one or two or more selected from a silicate and aluminum oxide, more preferably a silicate or aluminum oxide, further preferably a silicate, and furthermore preferably zirconium silicate.

<5>

The method for producing a catalyst according to any one of the above <1> to <4>, wherein the bimodal carrier has peaks of pore distribution in a range of 1 nm or more and 25 nm or less and a range of 30 nm or more and 200 nm or less, respectively.

<6>

The method for producing a catalyst according to any one of the above <1> to <5>, wherein in the pore distribution of the bimodal carrier, the peak position of pore distribution in the range of 1 nm or more and 25 nm or less lies at 1 nm or more, preferably 2 nm or more, and more preferably 3 nm or more, and lies at 25 nm or less, preferably 20 nm or less, more preferably 15 nm or less, further preferably 12 nm or less, furthermore preferably 10 nm or less, furthermore preferably 8 nm or less, furthermore preferably 6 nm or less, and furthermore preferably 5 nm or less.

<7>

The method for producing a catalyst according to any one of the above <1> to <6>, wherein in the pore distribution of the bimodal carrier, the peak position of pore distribution in the range of 30 nm or more and 200 nm or less lies at 30 nm or more, preferably 40 nm or more, more preferably 50 nm or more, and further preferably 55 nm or more, and lies at 200 nm or less, preferably 100 nm or less, more preferably 75 nm or less, and further preferably 65 nm or less.

<8>

The method for producing a catalyst according to any one of the above <1> to <7>, wherein the pore volume of the whole bimodal carrier is 0.2 mL/g or more, preferably 0.4 mL/g or more, more preferably 0.5 mL/g or more, further preferably 0.6 mL/g or more, and furthermore preferably 0.7 mL/g or more, and the pore volume is 1.5 mL/g or less, preferably 1 mL/g or less, and more preferably 0.9 mL/g or less.

<9>

The method for producing a catalyst according to any one of the above <1> to <8>, wherein the content of cobalt in the whole catalyst is 0.1% by mass or more, preferably 1% by mass or more, more preferably 5% by mass or more, and further preferably 7% by mass or more, and is 50% by mass or less, preferably 20% by mass or less, more preferably 15% by mass or less, and further preferably 10% by mass or less.

<10>

The method for producing a catalyst according to any one of the above <1> to <9>, wherein in the pore distribution of the catalyst, peak position ($d_1$) of pore distribution in the range of 1 nm or more and 25 nm or less lies at 1 nm or more, preferably 3 nm or more, more preferably 4 nm or more, further preferably 5 nm or more, and furthermore preferably 6 nm or more, and lies at 25 nm or less, preferably 20 nm or less, more preferably 15 nm or less, further preferably 14 nm or less, furthermore preferably 12 nm or less, furthermore preferably 10 nm or less, and furthermore preferably 8 nm or less.

<11>

The method for producing a catalyst according to any one of the above <1> to <10>, wherein in the pore distribution of the catalyst, the sum of pore volumes of pores forming peaks of pore distribution in the range of 1 nm or more and 25 nm or less is 0.02 mL/g or more, preferably 0.06 mL/g or more, more preferably 0.1 mL/g or more, further preferably 0.14 mL/g or more, and furthermore preferably 0.17 mL/g or more, and is 0.5 mL/g or less, preferably 0.3 mL/g or less, more preferably 0.2 mL/g or less, and further preferably 0.19 mL/g or less.

<12>

The method for producing a catalyst according to any one of the above <1> to <11>, wherein in the pore distribution of the catalyst, peak position ($d_2$) of pore distribution in the range of 30 nm or more and 200 nm or less lies at 30 nm or more, preferably 40 nm or more, more preferably 50 nm or more, and further preferably 55 nm or more, and lies at 200 nm or less, preferably 100 nm or less, more preferably 70 nm or less, and further preferably 65 nm or less.

<13>

The method for producing a catalyst according to any one of the above <1> to <12>, wherein in the pore distribution of the catalyst, the sum of pore volumes of pores forming peaks of pore distribution in the range of 30 nm or more and 200 nm or less is 0.1 mL/g or more, preferably 0.3 mL/g or more, more preferably 0.4 mL/g or more, and further preferably 0.45 mL/g or more, and is 1 mL/g or less, preferably 0.8 mL/g or less, more preferably 0.7 mL/g or less, further preferably 0.6 mL/g or less, and furthermore preferably 0.55 mL/g or less.

<14>

The method for producing a catalyst according to any one of the above <1> to <13>, wherein in the pore distribution of the catalyst, a ratio $d_1/d_2$ of peak position ($d_1$) of pore distribution in the range of 1 nm or more and 25 nm or less to peak position ($d_2$) of pore distribution in the range of 30 nm or more and 200 nm or less is 0.01 or more, preferably 0.05 or more, and more preferably 0.1 or more, and is 0.8 or less, preferably 0.4 or less, more preferably 0.19 or less, and further preferably 0.12 or less.

<15>

The method for producing a catalyst according to any one of the above <1> to <14>, wherein in the pore distribution of the catalyst, a ratio $V_1/V_2$ of pore volume ($V_1$) in the range of 1 nm or more and 25 nm or less to pore volume ($V_2$) in the range of 30 nm or more and 200 nm or less is 0.02 or more, preferably 0.05 or more, more preferably 0.1 or more, and further preferably 0.3 or more, and is 5 or less, preferably 1 or less, more preferably 0.5 or less, further preferably 0.38 or less, and furthermore preferably 0.35 or less.

<16>

The method for producing a catalyst according to any one of the above <1> to <15>, wherein the pore volume of the whole catalyst is 0.2 mL/g or more, preferably 0.4 mL/g or more, more preferably 0.5 mL/g or more, further preferably 0.6 mL/g or more, and furthermore preferably 0.7 mL/g or more, and is 1.5 mL/g or less, preferably 1 mL/g or less, and more preferably 0.9 mL/g or less.

<17>

The method for producing a catalyst according to any one of the above <1> to <16>, wherein the specific surface area of the whole catalyst is 10 m$^2$/g or more, preferably 100 m$^2$/g or more, more preferably 200 m$^2$/g or more, and further preferably 230 m$^2$/g or more, and is 1000 m$^2$/g or less, preferably 500 m$^2$/g or less, and more preferably 300 m$^2$/g or less.

<18>

The method for producing a catalyst according to any one of the above <1> to <17>, wherein step 1 includes the following steps:

step 1-1: supporting a dispersion or a solution containing a raw material of the porous layer on the porous material; and step 1-2: calcining the porous material with the dispersion or the solution supported thereon obtained in step 1-1.

<19>

The method for producing a catalyst according to the above <18>, wherein the raw material of the porous layer is supported by using an IW method in step 1-1.

<20>

The method for producing a catalyst according to the above <18> or <19>, wherein the raw material of the porous layer of step 1-1 is one or two or more selected from a silicate, silicon oxide, aluminum oxide, and zirconium oxide, preferably one or two or more selected from a silicate and aluminum oxide, more preferably a silicate or aluminum oxide, further preferably a silicate, and furthermore preferably zirconium silicate.

<21>

The method for producing a catalyst according to any one of the above <18> to <20>, wherein the temperature of the calcining of step 1-2 is 150° C. or more, preferably 200° C. or more, more preferably 250° C. or more, further preferably 300° C. or more, and furthermore preferably 400° C. or more, and is 1000° C. or less, preferably 900° C. or less, more preferably 800° C. or less, further preferably 700° C. or less, and furthermore preferably 600° C. or less.

<22>

The method for producing a catalyst according to any one of the above <18> to <21>, wherein the calcining of step 1-2 is performed in an oxygen-containing atmosphere, and preferably in an air atmosphere.

<23>

The method for producing a catalyst according to any one of the above <18> to <22>, wherein the calcining time of step 1-2 is 0 hour or more, preferably 0.5 hour or more, more preferably 1 hour or more, and further preferably 1.5 hours or more, and is 10 hours or less, preferably 8 hours or less, more preferably 6 hours or less, further preferably 4 hours or less, and furthermore preferably 2.5 hours or less.

<24>

The method for producing a catalyst according to any one of the above <1> to <23>, wherein the method for supporting cobalt which is a catalyst metal on the bimodal carrier in step 2 is a method for impregnating the bimodal carrier with a dispersion or a solution containing a cobalt compound, and preferably a method performed by using an IW method.

<25>

The method for producing a catalyst according to the above <24>, wherein the dispersion or the solution containing a cobalt compound of step 2 is a solution, a sol, or a slurry, and preferably a solution.

<26>

The method for producing a catalyst according to the above <24> or <25>, wherein the cobalt compound of step 2 is one or two or more selected from cobalt nitrate, cobalt acetate, cobalt sulfate, cobalt chloride, cobalt bromide, cobalt iodide, and cobalt oxide, preferably one or more selected from cobalt nitrate and cobalt acetate, and more preferably cobalt nitrate.

<27>

The method for producing a catalyst according to any one of the above <24> to <26>, wherein the bimodal carrier of step 2 is impregnated with the dispersion or the solution, and then calcined.

<28>

The method for producing a catalyst according to the above <27>, wherein the temperature of the calcining of step 2 is 150° C. or more, preferably 200° C. or more, more preferably 250° C. or more, and further preferably 300° C. or more, and is 800° C. or less, preferably 700° C. or less, more preferably 600° C. or less, and further preferably 500° C. or less.

<29>

The method for producing a catalyst according to the above <27> or <28>, wherein the calcining of step 2 is performed in an oxygen-containing atmosphere, and preferably in an air atmosphere.

<30>

The method for producing a catalyst according to any one of the above <27> to <29>, wherein the calcining time of step 2 is 0 hour or more, preferably 0.5 hour or more, more preferably 1 hour or more, and further preferably 1.5 hours or more, and is 10 hours or less, preferably 8 hours or less, more preferably 6 hours or less, further preferably 4 hours or less, and furthermore preferably 2.5 hours or less.

<31>

The method for producing a catalyst according to any one of the above <27> to <30>, wherein after the calcining of step 2, the catalyst is reduced by using a reducing agent.

<32>

The method for producing a catalyst according to the above <31>, wherein the reducing agent for the catalyst reduction of step 2 is mixed gas of carbon monoxide and hydrogen, or hydrogen gas, and preferably hydrogen gas.

<33>

A method for producing an alcohol having 8 or more and 22 or less carbon atoms including the following steps:

step 1: forming a porous layer on a surface of a porous material having a pore size mode of 30 nm or more and 200 nm or less to obtain a bimodal carrier;

step 2: supporting cobalt on the bimodal carrier obtained in step 1 to obtain a catalyst having peaks of pore distribution in a range of 1 nm or more and 25 nm or less and a range of 30 nm or more and 200 nm or less, respectively; and step 3: reacting carbon monoxide with hydrogen at a gauge pressure of 2 MPa or more and 100 MPa or less in the presence of the catalyst obtained in step 2.

<34>

The method for producing an alcohol having 8 or more and 22 or less carbon atoms according to the above <33>, wherein the constituent compound of the porous material is one or two or more selected from silicon oxide, a silicate, aluminum oxide, and titanium oxide, preferably one or two or more selected from silicon oxide, a silicate, and aluminum oxide, more preferably silicon oxide, a silicate, or aluminum oxide, and further preferably silicon oxide.

<35>

The method for producing an alcohol having 8 or more and 22 or less carbon atoms according to the above <33> or <34>, wherein the pore size mode of the porous material is 40 nm or more, preferably 50 nm or more, more preferably 55 nm or more, and further preferably 60 nm or more, and is 100 nm or less, preferably 80 nm or less, more preferably 75 nm or less, and further preferably 70 nm or less.

<36>

The method for producing an alcohol having 8 or more and 22 or less carbon atoms according to any one of the above <33> to <35>, wherein the content of cobalt in the whole catalyst is 0.1% by mass or more, preferably 1% by mass or more, more preferably 5% by mass or more, and further preferably 7% by mass or more, and is 50% by mass or less, preferably 20% by mass or less, more preferably 15% by mass or less, and further preferably 10% by mass or less.

<37>
The method for producing an alcohol having 8 or more and 22 or less carbon atoms according to any one of the above <33> to <36>, wherein in the pore distribution of the catalyst, peak position ($d_1$) of pore distribution in the range of 1 nm or more and 25 nm or less lies at 1 nm or more, preferably 3 nm or more, more preferably 5 nm or more, and further preferably 6 nm or more, and lies at 25 nm or less, preferably 20 nm or less, more preferably 15 nm or less, further preferably 12 nm or less, furthermore preferably 10 nm or less, and furthermore preferably 8 nm or less.
<38>
The method for producing an alcohol having 8 or more and 22 or less carbon atoms according to any one of the above <33> to <37>, wherein in the pore distribution of the catalyst, peak position ($d_2$) of pore distribution in the range of 30 nm or more and 200 nm or less lies at 30 nm or more, preferably 40 nm or more, more preferably 50 nm or more, and further preferably 55 nm or more, and lies at 200 nm or less, preferably 100 nm or less, more preferably 70 nm or less, and further preferably 65 nm or less.
<39>
The method for producing an alcohol having 8 or more and 22 or less carbon atoms according to any one of the above <33> to <38>, wherein the supply molar ratio $H_2/CO$ of hydrogen gas to carbon monoxide gas of step 3 is 0.8 or more, preferably 1.0 or more, more preferably 1.3 or more, further preferably 1.6 or more, and furthermore preferably 1.8 or more, and is 2.5 or less, preferably 2.4 or less, more preferably 2.3 or less, and further preferably 2.2 or less.
<40>
The method for producing an alcohol having 8 or more and 22 or less carbon atoms according to any one of the above <33> to <39>, wherein the apparatus in the reaction of step 3 is a slurry-bed reaction apparatus or a fixed-bed reaction apparatus, and preferably a slurry-bed reaction apparatus.
<41>
The method for producing an alcohol having 8 or more and 22 or less carbon atoms according to any one of the above <33> to <40>, wherein the gauge pressure in the reaction of step 3 is 3 MPa or more, preferably 4 MPa or more, more preferably 5 MPa or more, and further preferably 5.5 MPa or more, and is 50 MPa or less, preferably 30 MPa or less, more preferably 10 MPa or less, and further preferably 7 MPa or less.
<42>
The method for producing an alcohol having 8 or more and 22 or less carbon atoms according to any one of the above <33> to <41>, wherein a temperature in the reaction of step 3 is 100° C. or more, preferably 150° C. or more, more preferably 200° C. or more, and further preferably 230° C. or more, and is 300° C. or less, preferably 280° C. or less, more preferably 260° C. or less, and further preferably 250° C. or less.
<43>
The method for producing an alcohol having 8 or more and 22 or less carbon atoms according to any one of the above <33> to <42>, wherein in the reaction of step 3, atmospheric gas other than the raw material gases is inert gas, preferably nitrogen gas or rare gas, more preferably rare gas, and further preferably argon.
<44>
The method for producing an alcohol having 8 or more and 22 or less carbon atoms according to any one of the above <33> to <43>, wherein in the reaction of step 3, the content of the alcohol having 8 or more and 22 or less carbon atoms relative to the whole reaction product is 3% by mass or more, preferably 4% by mass or more, and more preferably 5% by mass or more, and is 100% by mass or less, preferably 50% by mass or less, more preferably 10% by mass or less, and further preferably 7% by mass or less.
<45>
A method for producing an alcohol having 8 or more and 22 or less carbon atoms including the step of reacting carbon monoxide with hydrogen at a gauge pressure of 2 MPa or more and 100 MPa or less in the presence of a catalyst obtained in the following steps 1 and 2:

step 1: forming a porous layer on a surface of a porous material having a pore size mode of 30 nm or more and 200 nm or less to obtain a bimodal carrier; and step 2: supporting cobalt on the bimodal carrier obtained in step 1 to obtain a catalyst having peaks of pore distribution in a range of 1 nm or more and 25 nm or less and a range of 30 nm or more and 200 nm or less, respectively.
<46>
A method for producing an alcohol having 8 or more and 22 or less carbon atoms including the step of reacting carbon monoxide with hydrogen at a gauge pressure of 2 MPa or more and 100 MPa or less in the presence of the catalyst obtained by the method for producing a catalyst according to any one of the above <1> to <31>.
<47>
The method for producing an alcohol having 8 or more and 22 or less carbon atoms according to the above <45> or <46>, wherein a temperature to react carbon monoxide with hydrogen is 100° C. or more and 300° C. or less.
<48>
The method for producing an alcohol having 8 or more and 22 or less carbon atoms according to any one of the above <45> to <47>, wherein the gauge pressure in the reaction between carbon monoxide and hydrogen is 4 MPa or more.

EXAMPLES

1. Evaluation Method (1) Reactivity and Selectivity
(i) Method for Analyzing Gas Component During Reaction A gas component during a reaction was introduced into a gas chromatograph (also referred to as GC) equipped with a thermal conductivity detector (also referred to as TCD) or a hydrogen flame ionization detector (also referred to as FID) through an outlet pipe from a reaction apparatus for every hour, to subject the gas component to GC analysis using argon as an internal standard substance.

The volume concentration of carbon monoxide in the gas component was calculated with an internal reference method using argon as an internal standard substance from a GC peak area % derived from carbon monoxide and a GC peak area % derived from argon. A calibration curve was prepared by measuring gases obtained by mixing standard gas containing carbon monoxide, methane, and carbon dioxide with argon, and plotting the peak area ratio of carbon monoxide and argon against the volume concentration ratio of carbon monoxide and argon at each mixing ratio.

The volume concentration of methane in the gas component was calculated with an internal reference method using argon as an internal standard substance from a GC peak area % derived from methane and a GC peak area % derived from argon. A calibration curve was prepared by measuring gases obtained by mixing standard gas containing carbon monoxide, methane, and carbon dioxide with argon at various mixing ratios, and plotting the peak area ratio of methane and argon against the volume concentration ratio of methane and argon at each mixing ratio.

The volume concentration of olefin in the gas component was obtained by the following equation.

$$\text{Volume concentration of olefin \%} = \text{Volume concentration of methane \%} \times \frac{\text{GC peak area derived from detected olefins having all numbers of carbon atoms}}{\text{GC peak area derived from detected methane}} \quad [\text{Equation 1}]$$

The volume concentration of paraffin in the gas component was obtained by the following equation.

$$\text{Volume concentration of paraffin \%} = \text{Volume concentration of methane \%} \times \frac{\text{GC peak area derived from detected paraffins having all numbers of carbon atoms}}{\text{GC peak area derived from detected methane}} \quad [\text{Equation 2}]$$

GC Measurement Conditions
(a) In the case of concentration analysis for carbon monoxide and methane
Amount of sample introduced: 1 mL
Gas chromatograph: "GC-320" (manufactured by GL Sciences Inc.)
Detector: TCD (embedded in the gas chromatograph)
Column: "Active Carbon" (manufactured by GL Sciences Inc., 60 to 80 mesh, column length: 3 m, column inner diameter: 2 mm)
Column temperature condition: 80° C.
Carrier gas: $N_2$
Inlet pressure: 200 kPa
Temperature of sample introduction part: 110° C.
Temperature of detector: 80° C.
(b) In the Case of Concentration Analysis for Olefin and Paraffin
Amount of sample introduced: 0.8 mL
Gas chromatograph: "GC-14B" (manufactured by Shimadzu Corporation)
Detector: FID (embedded in the gas chromatograph)
Column: "Porapak Q" (manufactured by GL Sciences Inc., filler mesh size: 80/100, column length: 3 m, column inner diameter: 2 mm)
Column temperature condition: 70° C. (0 min)->2° C./min->230° C. (0 min)
Carrier gas: $N_2$
Inlet pressure: 200 kPa
Temperature of sample introduction part: 200° C.
Temperature of detector: 230° C.
(ii) Analysis of Liquid Component of Reaction Product at End of Reaction After the end of the reaction, the reaction apparatus was cooled to 25° C., and a reactor and an ice trap each containing a product were then removed. The product in the ice trap was mixed in the reactor, and deionized water was added into the mixed solution to separate the mixed solution into an organic layer and a water layer.

To the organic layer, 0.1 g of 1-octanol (manufactured by Kanto Chemical Co., Inc.), 0.1 g of dodecane (manufactured by Kanto Chemical Co., Inc.) as internal standard substances were added, and to the water layer, 0.05 g of tertiary butanol (manufactured by Kanto Chemical Co., Inc.) was added, followed by sufficient stirring to obtain solutions. The solutions were then subjected to GC analysis. 0.2 µL of each sample was directly introduced to a GC to subject the sample to GC analysis.

The mass concentrations of alcohols in the organic layer were calculated with an internal reference method using 1-octanol as an internal standard substance from the sum of GC peak areas % derived from detected alcohols. A calibration curve was prepared by measuring a sample obtained by mixing a standard sample of each alcohol with 1-octanol, and plotting the peak area ratio of each alcohol and 1-octanol against the mass concentration ratio of each alcohol and 1-octanol.

The mass concentrations of olefins in the organic layer were calculated with an internal reference method using dodecane as an internal standard substance from the sum of GC peak areas % derived from detected olefins and a GC peak area % derived from dodecane. A calibration curve was prepared by measuring a sample obtained by mixing a standard sample of each olefin with dodecane, and plotting the peak area ratio of each olefin and dodecane against the mass concentration ratio of each olefin and dodecane.

The mass concentrations of paraffins in the organic layer were calculated with an internal reference method using dodecane as an internal standard substance from the sum of GC peak areas % derived from detected paraffins and a GC peak area % derived from dodecane. A calibration curve was prepared from the peak area ratio of each paraffin having a known concentration and dodecane having a known concentration and the concentration ratio of each paraffin and dodecane.

The mass concentrations of alcohols in the water layer were calculated with an internal reference method using tertiary butanol as an internal standard substance from the sum of GC peak areas % derived from detected alcohols and a GC peak area % derived from tertiary butanol. A calibration curve was prepared from the peak area ratio of each alcohol having a known concentration and tertiary butanol having a known concentration and the concentration ratio of each alcohol and tertiary butanol.

GC Measurement Conditions
Amount of sample introduced: 0.2 µL
Gas chromatograph: "GC-2014" (manufactured by Shimadzu Corporation)
Detector: FID (embedded in the gas chromatograph)
Column: "InertCap 5" (manufactured by GL Sciences Inc., column length: 30 m, column inner diameter: 0.25 mm)
Column temperature condition: 40° C. (5 min)->8° C./min->70° C. (1 min)->8° C./min->260° C. (5 min)->10° C./min->310° C. (20 min)->10° C./min->320° C. (9 min)
Carrier gas: $N_2$ 45 mL/min
Temperature of sample introduction part: 310° C.
Temperature of detector: 310° C.
(iii) Method for Calculating CO Conversion, ROH Selectivity, Olefin Selectivity, Paraffin Selectivity, and Number of Carbon Atoms of ROH The CO conversion, the ROH selectivity, the olefin selectivity, the paraffin selectivity, and the number of carbon atoms of ROH were calculated according to the following equations, respectively.

In the following equations, "c-mol" (also referred to as number of moles of carbon atoms) is the number of moles of carbon atoms in each component, and is represented by the following equations. "c-mol %" (also referred to as carbon mol %) is the proportion of the number of moles of carbon atoms of each product to the number of moles of carbon atoms of all products, and is represented by the following equations. The total amount of olefins generated, the total amount of paraffins generated, the total amount of HC generated, the total amount of ROH generated, the CO conversion, the ROH selectivity, the olefin selectivity, the paraffin selectivity, and the number of carbon atoms of ROH were calculated from the following equations.

$$\text{Number of moles of carbon atoms} = \quad \text{[Equation 3]}$$
$$\text{Number of moles of each component} \times$$
$$\text{Number of carbon atoms in each component}$$

$$\text{Carbon mol \%} = \frac{\text{Number of moles of carbon atoms of each product}}{\text{Number of moles of carbon atoms of all products}} \times 100$$

$$\text{Total amount of olefin generated (c-mol)} = \text{Sum of the numbers of moles of carbon atoms of generated olefins having all numbers of carbon atoms}$$

$$\text{Total amount of paraffin generated (c-mol)} = \text{Sum of the numbers of moles of carbon atoms of generated paraffins having all numbers of carbon atoms}$$

$$\text{Total amount of HC generated (c-mol)} =$$
$$\text{Total amount of olefin generated (c-mol)} +$$
$$\text{Total amount of paraffin generated (c-mol)}$$

$$\text{Total amount of ROH generated (c-mol)} = \text{Sum of the numbers of moles of carbon atoms of generated alcohols having all numbers of carbon atoms}$$

$$\text{CO Conversion (mol \%)} =$$
$$\left\{ 1 - \left( \frac{\text{Concentration of carbon monoxide in gas component at outlet of reactor (mol \%)}}{\text{Concentration of carbon monoxide in gas supplied to reactor (mol \%)}} \right) \right\} \times 100$$

$$\text{ROH selectivity (c-mol \%)} =$$
$$\frac{\text{Total amount of ROH generated (c-mol)}}{\text{Total amount of ROH generated (c-mol)} + \text{Total amount of HC generated (c-mol)}} \times 100$$

$$\text{Olefin selectivity (c-mol \%)} =$$
$$\frac{\text{Total amount of olefin generated (c-mol)}}{\text{Total amount of ROH generated (c-mol)} + \text{Total amount of HC generated (c-mol)}} \times 100$$

$$\text{Paraffin selectivity (c-mol \%)} =$$
$$\frac{\text{Total amount of paraffin generated (c-mol)}}{\text{Total amount of ROH generated (c-mol)} + \text{Total amount of HC generated (c-mol)}} \times 100$$

$$\text{Number of carbon atoms of ROH (c-mol \%)} =$$
$$\frac{\text{Amount generated ROH having each number of carbon atoms (c-mol)}}{\text{Total amount of ROH generated (c-mol)}} \times 100$$

(2) Composition of Catalyst

After 0.1 g of a catalyst and 2 g of an alkali flux were collected in a platinum crucible, the platinum crucible was heated to 950° C. to melt the content. After the platinum crucible was naturally cooled at 25° C., 10 mL of a mixed solution of hydrochloric acid and ultrapure water was added into the platinum crucible, and the platinum crucible was then heated to 70° C. or more and 80° C. or less to dissolve the content. After the platinum crucible was naturally cooled at 25° C., the volume of the content was set to 100 mL by ultrapure water. An aqueous solution obtained by setting the volume was used as a sample.

A solution for preparing a calibration curve was prepared by adding hydrochloric acid, an alkali flux, and ultrapure water to a cobalt standard solution so that the concentration of hydrogen chloride was set to 0.6 mol/L, and the concentration of an alkali flux was set to 2% by mass.

The sample and the solution for preparing a calibration curve were measured with ICP-AEP, and the content of cobalt in the catalyst was calculated from the concentration of cobalt in the obtained sample.

An ICP emission spectrometer "iCAP6500Duo" (manufactured by Thermo Fisher Scientific K.K.) was used for measurement of the concentration of cobalt by ICP-AEP.

The alkali flux used was obtained by mixing sodium carbonate (manufactured by Wako Pure Chemical Industries, Ltd., special grade) with boric acid (manufactured by Wako Pure Chemical Industries, Ltd., special grade) at sodium carbonate: boric acid (mass ratio)=1:0.4. The mixed solution of hydrochloric acid and ultrapure water used was obtained by mixing hydrochloric acid with ultrapure water at hydrochloric acid: ultrapure water (volume ratio)=1:1. The hydrochloric acid used was hydrochloric acid (manufactured by Kanto Chemical Co., Inc., for atomic absorption spectrometry). The cobalt standard solution used was 1000 mg/L of a standard solution for atomic absorption spectrometry (manufactured by Kanto Chemical Co., Inc.).

(3) Method for Measuring Pore Structure

The pore size modes, the pore distributions, the specific surface areas, and the pore volumes of the catalyst and the bimodal carrier were calculated from an adsorption-desorption isotherm obtained by a nitrogen adsorption method performed at 119 points at a relative pressure $P/P_0$ of 0 to 0.995 using an automatic gas adsorption apparatus "AUTOSORB-1" (manufactured by Quantachrome Corporation) at −197° C. The catalyst and the bimodal carrier were dried under reduced pressure at 200° C. for 2 hours, and then measured. Herein, P is an adsorption equilibrium pressure during measurement, and $P_0$ is the saturated vapor pressure of nitrogen at a measurement temperature.

2. Production Example of Bimodal Carrier (1) Porous Material

In the production example of the bimodal carrier according to the present invention, the porous material used was a silica carrier "CARiACT Q-50" (pore size mode: 65 nm, manufactured by Fuji Silysia Chemical Ltd.).

(2) Raw Material of Porous Layer

In the production example of the bimodal carrier according to the present invention, as the raw material of the porous layer, a sol containing zirconium silicate as a main component was used, the sol being named "CERAMIC G-401" (manufactured by Kabushikikaisha Nippan Kenkyusho, solid content concentration: 16% by mass (LOT number: 31118), 21% by mass (LOT number: 31022), solvent: isopropyl alcohol).

(3) Production Example of Bimodal Carrier (Step 1)

Bimodal Carrier a (Step 1-1)

5 g of a silica carrier was impregnated with the zirconium silicate sol under conditions of 25° C. and an atmospheric pressure over 1 hour by the IW method while the silica carrier was ultrasonically vibrated. The zirconium silicate sol used was obtained by adding 1 mL of isopropanol (manufactured by Kanto Chemical Co., Inc.) to 7.81 g of "CERAMIC G-401" (LOT number: 31118).

(Step 1-2)

After the impregnation, the silica carrier was left to stand under reduced pressure with an aspirator at 25° C. for 1 hour. Then, the silica carrier was dried at 120° C. in an air atmosphere under an atmospheric pressure overnight. After drying, the temperature of the silica carrier was increased to 400° C. at 2° C./min in an air atmosphere under an atmospheric pressure using a muffle furnace, and held at 400° C. for 2 hours to calcine the silica carrier. Then, the silica carrier was cooled to 25° C. in an air atmosphere under an atmospheric pressure to obtain bimodal carrier a. The physical property values of obtained bimodal carrier a are shown in Table 1.

Bimodal Carrier b

Bimodal carrier b was obtained in the same manipulation as in the production example of bimodal carrier a except that, in the production example of bimodal carrier a, a silica carrier was impregnated with a zirconium silicate sol obtained by adding 0.45 g of poly(ethylene glycol)-block-poly(propylene glycol)-block-poly(ethylene glycol) "Pluronic P123" (manufactured by BASF A.G., molecular weight: 5800, the number of moles of added ethylene oxy groups: 20, the number of moles of added propylene oxy groups: 70, the number of moles of added ethylene oxy groups: 20), and 1 mL of isopropanol (manufactured by Kanto Chemical Co., Inc.) to 7.81 g of "CERAMIC G-401" (LOT number: 31118), and a calcining temperature was changed to 600° C. from 400° C. The physical property values of obtained bimodal carrier b are shown in Table 1.

Bimodal Carrier c

A zirconium silicate sol was used, which was obtained by adding 0.61 g of poly(ethylene glycol)-block-poly(propylene glycol)-block-poly(ethylene glycol) "Pluronic P123" (manufactured by BASF A.G., molecular weight: 5800, the number of moles of added ethylene oxy groups: 20, the number of moles of added propylene oxy groups: 70, the number of moles of added ethylene oxy groups: 20) and 2.5 mL of isopropanol (manufactured by Kanto Chemical Co., Inc.) to 10.2 g of "CERAMIC G-401" (LOT number: 31022).

5 g of a silica carrier was impregnated with a half amount of the zirconium silicate sol under an atmospheric pressure at 25° C. over 1 hour while the silica carrier was ultrasonically vibrated. After the impregnation, the same manipulation as in step 1-2 of bimodal carrier a was performed except that the calcining temperature was changed to 600° C. from 400° C. in step 1-2 of bimodal carrier a.

The obtained powder was further impregnated with the remaining half amount of the zirconium silicate sol under an atmospheric pressure at 25° C. over 1 hour while the powder was ultrasonically vibrated. After the impregnation, bimodal carrier c was obtained in the same manipulation as in step 1-2 of bimodal carrier a except that the calcining temperature was changed to 600° C. from 400° C. in step 1-2 of bimodal carrier a. The physical property values of obtained bimodal carrier c are shown in Table 1.

TABLE 1

|  | Bimodal carrier a | Bimodal carrier b | Bimodal carrier c |
| --- | --- | --- | --- |
| Amount of $ZrSiO_4$ supported with respect to 100 parts by mass of silica carrier (parts by mass) | 25 | 25 | 43 |
| Peak position in small pore range (nm) | 4 | 10 | 17 |
| Peak position in large pore range (nm) | 57 | 55 | 62 |
| Total pore volume (mL/g) | 0.82 | 0.78 | 0.80 |

3. Production Example of Cobalt Supported Catalyst (Step 2)

Example 1 (Co Supported Catalyst A)

3 g of bimodal carrier a was impregnated with a cobalt nitrate aqueous solution under conditions of 25° C. and an atmospheric pressure over 1 hour by the IW method while bimodal carrier a was ultrasonically vibrated. The cobalt nitrate aqueous solution used was obtained by dissolving 1.65 g of cobalt(II) nitrate hexahydrate (manufactured by Kanto Chemical Co., Inc.) in 1.85 mL of deionized water.

After the impregnation, bimodal carrier a was left to stand at 25° C. under reduced pressure with an aspirator for 1 hour. Then, bimodal carrier a was dried at 120° C. in an air atmosphere under an atmospheric pressure overnight. After drying, the temperature of bimodal carrier a was increased to 400° C. at 2° C./min in an air atmosphere under an atmospheric pressure using a muffle furnace, and held at 400° C. for 2 hours for calcining. The calcined catalyst was left to stand as it is in a reduction furnace. After air in the muffle furnace was replaced by nitrogen, the temperature of the catalyst was increased to 400° C. over 3 hours in a state where 100° 1 hydrogen was aerated at 80 mL/min under an atmospheric pressure in the muffle furnace, and held at 400° C. for 10 hours for reduction.

After the end of the reduction, the atmosphere was switched to nitrogen, and the catalyst was cooled to 25° C. Then, nitrogen containing 1% by volume of oxygen was aerated at 15 mL/min in the muffle furnace, to perform a surface immobilization treatment until oxygen absorption was no longer observed, thereby obtaining Co supported catalyst A. The physical property values of obtained Co supported catalyst A are shown in Table 2.

Example 2 (Co Supported Catalyst B)

Co supported catalyst B was obtained in the same manipulation as in the production example of Co supported catalyst A except that 3 g of bimodal carrier b was impregnated with a cobalt nitrate aqueous solution obtained by dissolving 1.65 g of cobalt(II) nitrate hexahydrate (manufactured by Kanto Chemical Co., Inc.) in 1.72 mL of deionized water over 1 hour by the IW method while bimodal carrier b was ultrasonically vibrated. The physical property values of obtained Co supported catalyst B are shown in Table 2.

Comparative Example 1 (Co Supported Catalyst C)

Co supported catalyst C was obtained in the same manipulation as in the production example of Co supported catalyst A except that 3 g of bimodal carrier c was impregnated with a cobalt nitrate aqueous solution obtained by dissolving 1.65 g of cobalt(II) nitrate hexahydrate (manufactured by Kanto Chemical Co., Inc.) in 1.72 mL of deionized water over 1 hour by the IW method while bimodal carrier c was ultrasonically vibrated. The physical property values of obtained Co supported catalyst C are shown in Table 2.

In Co supported catalyst C, peaks of adsorption-desorption isotherms derived from a small pore and a large pore obtained by a nitrogen adsorption method overlapped with each other. Therefore, the pore volumes of the small pore and the large pore could not be obtained. Table 2 shows that the pore volumes are "unmeasurable."

Comparative Example 2 (Co Supported Catalyst D)

Co supported catalyst D was obtained in the same manipulation as in the production example of Co supported catalyst A except that 5 g of the silica carrier "CARiACT Q-50" was impregnated with a cobalt nitrate aqueous solution obtained by dissolving 2.79 g of cobalt(II) nitrate hexahydrate (manufactured by Kanto Chemical Co., Inc.) in 5.27 mL of deionized water over 1 hour by the IW method while the silica carrier was ultrasonically vibrated. The physical property values of obtained Co supported catalyst D are shown in Table 2. In Table 2, Co supported catalyst D has no small pore, which shows that the peak position of a small pore range and the pore volume are "undetected".

TABLE 2

|  | Co supported catalyst A | Co supported catalyst B | Co supported catalyst C | Co supported catalyst D |
|---|---|---|---|---|
| Peak position in small pore range ($d_1$) (nm) | 6.7 | 11.5 | 35 | Undetected |
| Pore volume of small pore ($V_1$) (mL/g) | 0.17 | 0.19 | Unmeasurable | Undetected |
| Peak position in large pore range ($d_2$) (nm) | 59.0 | 59.3 | 59.7 | 58.6 |
| Pore volume of large pore ($V_2$) (mL/g) | 0.52 | 0.50 | Unmeasurable | 1.5 |
| $d_1/d_2$ (ratio) | 0.11 | 0.19 | 0.59 | — |
| $V_1/V_2$ (ratio) | 0.33 | 0.38 | — | — |
| Total pore volume (mL/g) | 0.75 | 0.82 | 0.67 | 1.5 |
| Total specific surface area (m$^2$/g) | 233 | 297 | 203 | 170 |
| Co content (% by mass) | 8.5 | 8.5 | 8.7 | 9.2 |

4. Step of Reacting Carbon Monoxide with Hydrogen (1) Reaction Manipulation

The reactor of the reaction apparatus used was a semi batch type autoclave having an inner volume of 80 mL. 20 mL of n-hexadecane (manufactured by Kanto Chemical Co., Inc.) and 0.5 g of the ground catalyst were placed in the reactor, and a gauge pressure was increased to 6.0 MPa. Gas ($H_2$/CO (mole ratio)=2, hydrogen content=65% by volume, carbon monoxide content=32% by volume, argon content=3% by volume) was flowed at 40 mL/min (the mass (W/F) of the charged catalyst to the number of moles of hydrogen and carbon monoxide supplied per hour=5 g·h/mol), and the temperature was increased to 240° C. from 25° C. over 1 hour and 20 minutes. The time when the temperature reached 240° C. was taken as reaction onset. At this time, the contents in the reactor were stirred at the rotation number of 1200 rpm. The selection catalysts, the reaction conditions, and the reaction results of Examples and Comparative Examples are shown in Table 3.

TABLE 3

| | | | Examples | | Cmparative Examples | | |
|---|---|---|---|---|---|---|---|
| | | | 1 | 2 | 1 | 2 | 3 |
| Reaction conditions | | Catalyst | Co supported catalyst A | Co supported catalyst B | Co supported catalyst C | Co supported catalyst D | Co supported catalyst A |
| | | Reaction Temperature (° C.) | 240 | 240 | 240 | 240 | 240 |
| | | Gauge pressure (MPa) | 6 | 6 | 6 | 6 | 1 |
| | | Reaction time (h) | 17 | 17 | 17 | 17 | 17 |
| | | Stirring speed (rpm) | 1200 | 1200 | 1200 | 1200 | 1200 |
| | | Supply molar ratio of $H_2$/CO | 2 | 2 | 2 | 2 | 2 |
| | Composition of raw material gas | hydrogen content (% by volume) | 65 | 65 | 65 | 65 | 65 |
| | | carbon monoxide content (% by volume) | 32 | 32 | 32 | 32 | 32 |
| | | Argon content (% by volume) | 3 | 3 | 3 | 3 | 3 |
| | | Raw material gas supply flow rate (mL/min) | 40 | 40 | 40 | 40 | 40 |
| | | Amount of catalyst loaded (g) | 0.5 | 0.5 | 0.5 | 0.5 | 0.5 |
| | | Solvent type | n-hexadecane | n-hexadecane | n-hexadecane | n-hexadecane | n-hexadecane |
| | | Amount of solvent loaded (mL) | 20 | 20 | 20 | 20 | 20 |
| Evaluation results | | CO conversion (mol %) | 12 | 11 | 37 | 34 | 70 |
| | | ROH selectivity (c-mol %) | 5 | 9 | 7 | 7 | 0 |
| | Number of carbon atoms of ROH (c-mol %) | Amount of generated ROH having 1 to 7 carbon atoms | 2 | 23 | 46 | 39 | Undetected |
| | | Amount of generated ROH having 8 to 22 carbon atoms | 89 | 67 | 48 | 55 | Undetected |
| | | Amount of generated ROH having 23 or more carbon atoms | 9 | 10 | 6 | 6 | Undetected |

TABLE 3-continued

| | Examples | | Cmparative Examples | | |
|---|---|---|---|---|---|
| | 1 | 2 | 1 | 2 | 3 |
| Olefin selectivity (c-mol %) | 33 | 40 | 31 | 35 | 16 |
| Paraffine selectivity (c-mol %) | 62 | 51 | 62 | 57 | 80 |

In Table 3, "undetected" shows that the amount of generated ROH having each number of carbon atoms cannot be detected.

The contrast of Examples 1 and 2 with Comparative Examples 1 and 2 shows that an alcohol having 8 or more and 22 or less carbon atoms can be selectively produced in the production of an aliphatic alcohol using a syngas as a raw material according to the catalyst of the present invention.

The contrast of Example 1 with Comparative Example 3 shows that an alcohol having 8 or more and 22 or less carbon atoms can be selectively produced in the production of an aliphatic alcohol using a syngas as a raw material according to the catalyst of the present invention and the specific reaction pressure.

The invention claimed is:

1. A method for producing an alcohol having 8 or more and 22 or less carbon atoms comprising the following steps:
   step 1: forming a porous layer on a surface of a porous material having a pore size mode of 30 nm or more and 200 nm or less to obtain a bimodal carrier,
   step 2: supporting cobalt on the bimodal carrier obtained in step 1 to obtain a catalyst having peaks of pore distribution in a range of 1 nm or more and 25 nm or less and a range of 30 nm or more and 200 nm or less, respectively; and
   step 3: reacting carbon monoxide with hydrogen at a gauge pressure of 2 MPa or more and 100 MPa or less in the presence of the catalyst obtained in step 2.

2. The method for producing an alcohol having 8 or more and 22 or less carbon atoms according to claim 1, wherein the porous layer contains one or two or more selected from a silicate, silicon oxide, aluminum oxide, and zirconium oxide.

3. The method for producing an alcohol having 8 or more and 22 or less carbon atoms according to claim 1, wherein step 1 comprises the following steps:
   step 1-1: supporting a dispersion or a solution containing a raw material of the porous layer on the porous material; and
   step 1-2: calcining the porous material with the dispersion or the solution supported thereon obtained in step 1-1.

4. The method for producing an alcohol having 8 or more and 22 or less carbon atoms according to claim 1, wherein the porous material contains silicon oxide.

5. The method for producing an alcohol having 8 or more and 22 or less carbon atoms according to claim 1, wherein the reaction temperature in step 3 is 100° C. or more and 300° C. or less.

6. The method for producing an alcohol having 8 or more and 22 or less carbon atoms according to claim 1, wherein in the pore distribution of the catalyst, the peak position of pore distribution is in the range of 4 nm or more and 14 nm or less.

7. The method for producing an alcohol having 8 or more and 22 or less carbon atoms according to claim 1, wherein in the pore distribution of the catalyst, the peak position of pore distribution in the range of 40 nm or more and 200 nm or less.

8. The method for producing an alcohol having 8 or more and 22 or less carbon atoms according to claim 1, wherein the gauge pressure in the reaction in step 3 is 4 MPa or more.

9. A method for producing an alcohol having 8 or more and 22 or less carbon atoms comprising a step of reacting carbon monoxide with hydrogen at a gauge pressure of 2 MPa or more and 100 MPa or less in the presence of the catalyst obtained by forming a porous layer on a surface of a porous material having a pore size mode of 50 nm or more and 100 nm or less to obtain a bimodal carrier and supporting cobalt on said bimodal carrier to obtain a catalyst having peaks of pore distribution in a range of 3 nm or more to 15 nm or less and a range of 50 nm or more to 100 nm or less, respectively.

10. The method for producing an alcohol having 8 or more and 22 or less carbon atoms according to claim 9, wherein a temperature to react carbon monoxide with hydrogen is 100° C. or more and 300° C. or less.

11. The method for producing an alcohol having 8 or more and 22 or less carbon atoms according to claim 9, wherein the gauge pressure in the reaction between carbon monoxide and hydrogen is 4 MPa or more.

* * * * *